United States Patent [19]
Baker et al.

[11] Patent Number: 6,080,109
[45] Date of Patent: *Jun. 27, 2000

[54] MODULAR IMAGING/TREATMENT CATHETER ASSEMBLY

[75] Inventors: Bruce A. Baker, Placerville; Clifford R. Varney, El Dorado Hills; Michael J. Eberle, Fair Oaks, all of Calif.

[73] Assignee: Endosonics Corporation, Rancho Cordova, Calif.

[ * ] Notice: This patent is subject to a terminal disclaimer.

[21] Appl. No.: 09/234,967

[22] Filed: Jan. 21, 1999

Related U.S. Application Data

[63] Continuation of application No. 08/987,465, Dec. 9, 1997, Pat. No. 5,876,344.

[51] Int. Cl.[7] ............................................. A61B 8/12
[52] U.S. Cl. ............................................. 600/463; 600/439
[58] Field of Search .................................. 600/439, 459, 600/462–463, 466–467, 471, 585

[56] References Cited

U.S. PATENT DOCUMENTS

| | | |
|---|---|---|
| 4,841,977 | 6/1989 | Griffith et al. . |
| 4,917,097 | 4/1990 | Proudian et al. ................ 600/466 |
| 5,167,233 | 12/1992 | Eberle et al. . |
| 5,363,853 | 11/1994 | Lieber et al. . |
| 5,368,037 | 11/1994 | Eberle et al. . |
| 5,370,615 | 12/1994 | Johnson . |
| 5,372,138 | 12/1994 | Crowley et al. ................ 600/471 |
| 5,603,327 | 2/1997 | Eberle et al. . |
| 5,779,644 | 7/1998 | Eberle et al. . |
| 5,876,344 | 3/1999 | Baker et al. ................ 600/463 |

FOREIGN PATENT DOCUMENTS

| | | |
|---|---|---|
| 699451 | 3/1996 | European Pat. Off. . |
| 93 17750 | 9/1993 | WIPO . |
| 96 00099 | 1/1996 | WIPO . |

*Primary Examiner*—Francis J. Jaworski
*Attorney, Agent, or Firm*—Flehr Hohbach Test Albritton & Herbert LLP

[57] ABSTRACT

Catheter assembly in which an imaging transducer is positioned proximally of a treatment device at the distal end of a catheter. Unrestricted flow between a fluid lumen in the catheter and the treatment device is provided by an annular passageway formed between the walls of a marker tube which extends through the transducer and a guide wire tube which passes through the marker tube, and by a plenum chamber which is formed between the distal end of the catheter and the proximal end of the marker tube in communication with the fluid lumen and the flow passageway. The catheter, the treatment device, and the transducer are all constructed as individual modular units which can be assembled together as desired to form the assembly.

11 Claims, 2 Drawing Sheets

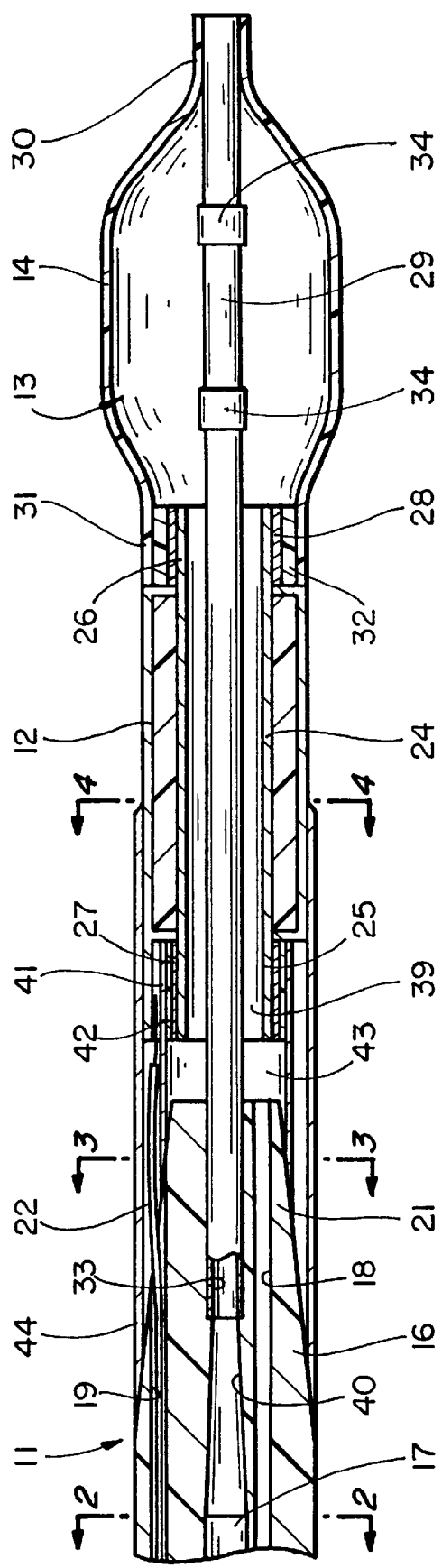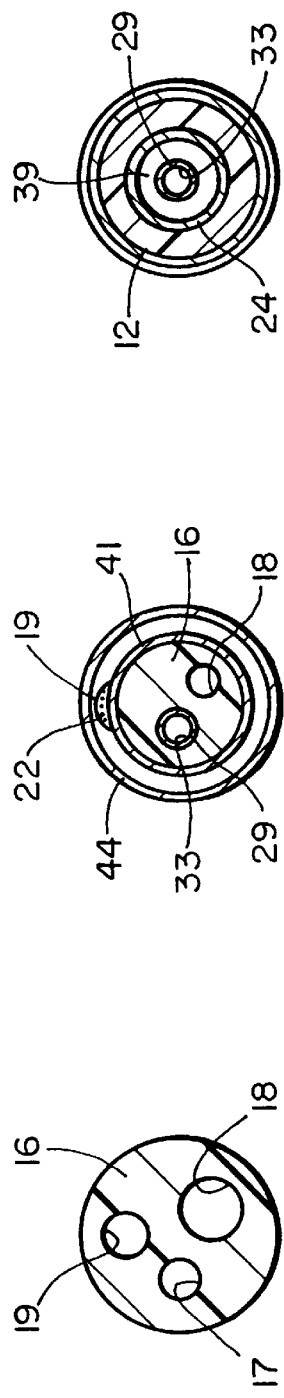

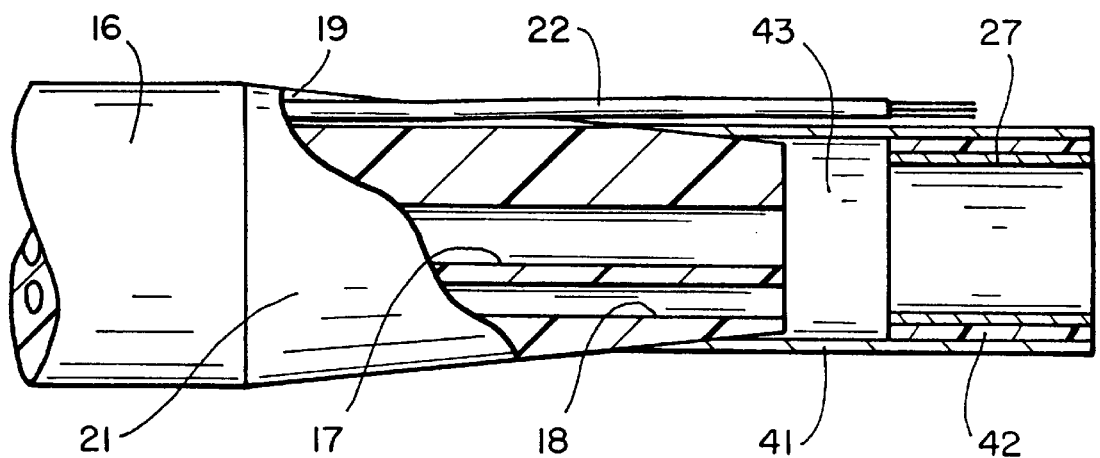
FIG_5
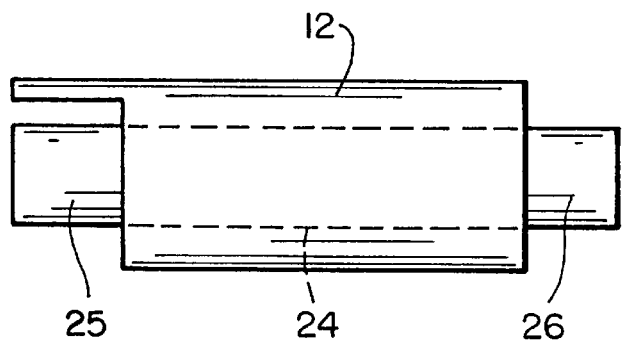
FIG_6
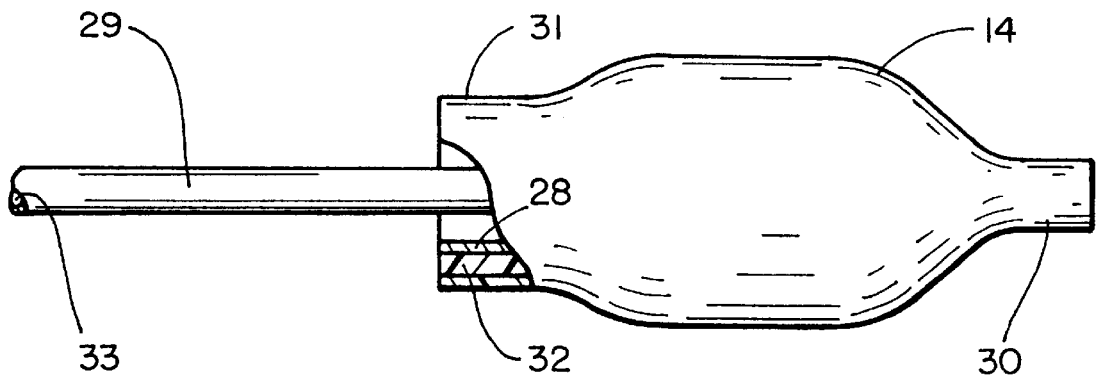
FIG_7

MODULAR IMAGING/TREATMENT CATHETER ASSEMBLY

CROSS-REFERENCE TO RELATED APPLICATION

This is a continuation of Ser. No. 08/987,465, filed Dec. 9, 1997 and now U.S. Pat. No. 5,876,344.

FIELD OF INVENTION

This invention pertains generally to medical devices and, more particularly, to a catheter assembly for use in applications such as ultrasonic imaging and percutaneous transluminal coronary angioplasty (PTCA).

BACKGROUND OF THE INVENTION

In recent years, intravascular ultrasound (IVUS) imaging systems have been developed for use in the diagnosis and treatment of cardiovascular and peripheral vascular disease. Such systems generally have one or more miniaturized transducers mounted on the tip of a catheter to provide electronic signals to an external imaging system in order to produce an image of the lumen of the artery or other vessel into which the catheter is inserted, the tissue of the vessel, and/or the tissue surrounding the vessel. These systems provide important diagnostic information which is not available from other more conventional techniques such as x-ray angiography. This information includes the location, amount and composition of arteriosclerotic plaque, and enables physicians to identify lesion characteristics, select an optimum course of treatment, position therapeutic devices and promptly assess the results of treatment.

Transluminal angioplasty utilizes an inflatable balloon at the distal end of an elongated flexible catheter to eliminate a blockage, or stenosis, produced by an accumulation of fatty tissue, or plaque, on the inner wall of a blood vessel or artery. The catheter is inserted into the vascular system and advanced along a guide wire to position the balloon next to the stenosis. When the balloon is properly positioned, it is inflated with pressurized fluid to compress the plaque and thereby relieve the stenosis.

The location of the stenosis and the positioning of the balloon were originally determined by techniques such as x-ray angiography and fluoroscopy wherein a radiopaque dye is injected into the vessel and radiopaque markers are mounted on the balloon, and x-ray imaging is employed to determine the location of the narrowing and the position of the balloon.

More recently, ultrasonic imaging has been used in combination with angioplasty in order to provide more detailed information about the stenosis. In one such technique, two separate catheters are employed, one having an ultrasonic imaging device at it distal end, the other having an inflatable balloon at its distal end. The balloon catheter is inserted along a guide wire and positioned by conventional techniques, and the balloon is inflated to treat the stenosis. That catheter is then removed, and the imaging catheter is inserted to enable the physician to examine the stenosis and determine if further treatment is needed. This technique does provide more information about the stenosis, but it requires an exchange of catheters and does not permit real time imaging of the dilation procedure.

Heretofore, there have also been some attempts to combine an ultrasonic imaging device and an inflatable balloon on a single catheter. With this approach, the imaging transducer can be used in the positioning of the balloon, the need to exchange catheters is eliminated, and the transducer can provide real time imaging of the dilation procedure, as well as images of the affected region after the treatment.

One problem with having the transducer and the balloon on a single catheter is that the transducer, being larger in profile than the deflated balloon, can prevent the balloon from being deployed in narrower stenosis. This is particularly so when the transducer is positioned distally of the balloon.

U.S. Pat. No. 5,167,233 describes a catheter in which the transducer is positioned proximally of the balloon. This permits the balloon to be inserted into stenoses which would be too narrow to be treated if the transducer had to pass through them first. However, having the transducer proximal to the balloon does present a problem in that the pressurized fluid must flow past the transducer, both during inflation and during deflation of the balloon. If the flow path is unduly restricted, inflation and deflation of the balloon will be undesirably slow.

OBJECTS AND SUMMARY OF THE INVENTION

It is in general an object of the invention to provide a new and improved catheter assembly in which an ultrasonic imaging transducer and a treatment device are mounted on a single catheter.

Another object of the invention is to provide a catheter assembly of the above character in which the transducer is positioned proximally of the treatment device without undue restriction of the flow of fluid to and from the treatment device.

Another object of the invention is to provide a catheter assembly of the above character in which the construction of the assembly is modular.

These and other objects are achieved in accordance with the invention by providing catheter assembly comprising a catheter having a guide wire lumen and a fluid lumen which open through a distal end thereof, an ultrasound imaging transducer positioned distally of the catheter and having a flow passageway, and a plenum chamber which provides communication between the fluid lumen in the catheter and the flow passageway in the transducer. A treatment device having an axially extending guide wire tube is connected to the distal end of the catheter in alignment with the guide wire lumen to form a continuous passageway for a guide wire. The catheter, the transducer, and the treatment device are all constructed as individual modular units which can be assembled together as desired to form the assembly.

BRIEF DESCRIPTION OF THE DRAWINGS

FIG. 1 is fragmentary centerline sectional of one embodiment of a catheter assembly incorporating the invention.

FIG. 2 is a cross-sectional view taken along line 2—2 in FIG. 1.

FIG. 3 is a cross-sectional view taken along line 3—3 in FIG. 1.

FIG. 4 is a cross-sectional view taken along line 4—4 in FIG. 1.

FIG. 5 is an enlarged side elevational view, partly broken away, of the distal end portion of the catheter in the embodiment of FIG. 1.

FIG. 6 is a side elevational view of the transducer and marker tube in the embodiment of FIG. 1.

FIG. 7 is a side elevational view of the treatment device and guide wire tube in the embodiment of FIG. 1.

DETAILED DESCRIPTION

As illustrated in the drawings, the assembly includes a catheter 11, an ultrasonic imaging transducer 12, and a treatment device 13 in the form of an inflatable angioplasty balloon 14.

The catheter has an elongated flexible shaft 16, with a guide wire lumen 17, a fluid lumen 18, and a cable lumen 19 extending longitudinally thereof. At its proximal end, the catheter can be connected to a conventional device such as a tri-arm adapter (not shown) which provides communication between the three lumens and devices associated therewith, e.g. a steering device or controller for the guide wire, a source of pressurized fluid for the treatment device, and a signal processor and display for the transducer.

The distal end portion 21 of catheter shaft 16 is tapered, with guide wire lumen 17 and fluid lumen 18 opening through the distal end of the shaft, and cable lumen 19 opening through the tapered side wall.

In one presently preferred embodiment, the catheter is fabricated of a polymeric material such as nylon which is extruded to form the three lumens, with the fluid lumen 18 being made as large as possible in order to maximize flow efficiency to and from the treatment device.

Ultrasonic imaging device 12 and the signal processing and imaging circuitry associated with it can be of the type shown in U.S. Pat. No. 4,917,097, the disclosure of which is incorporated herein by reference. It has a plurality of transducer elements arranged in a generally circular array centered about the axis, with circuitry for sequentially addressing the elements to provide an electronically scanned field of view. Connections to the transducer are made by a multi-conductor cable 22 which extends through cable lumen 19 in the catheter.

A metal marker tube 24 extends coaxially of the transducer, with end portions 25, 26 of the tube projecting from the proximal and distal ends of the transducer. In a presently preferred embodiment, the marker tube and the transducer are fabricated as a modular unit, with the tube being permanently bonded to the transducer. Marker bands 27, 28 of radiopaque material are disposed coaxially about the projecting portions of the tube.

Balloon 14 is mounted on a guide wire tube 29 which extends proximally from the balloon. The distal end portion 30 of the balloon is sealed directly to the outer wall of the tube, and the proximal end portion comprises a sleeve 31 of greater diameter for connection to the transducer. Marker band 28 is disposed coaxially within sleeve 31, with a spacer 32 between the marker band and the sleeve. These elements are heat sealed together, with the spacer serving as a matching element which seals well with both the metal marker band and the balloon. In a presently preferred embodiment, the balloon is fabricated of nylon, and the spacer is a co-extrusion having an inner layer of polyethylene which bonds well with the metal and an outer layer of nylon which bonds well with the balloon.

The guide wire tube is also formed as a co-extrusion, with an inner layer of polyethylene and an outer layer of nylon. The polyethylene is more lubricous than nylon, and a guide wire will slide through it better than through nylon. The nylon, however, bonds better with the balloon and with the shaft of the catheter.

The guide wire tube has an axially extending passageway or lumen 33 which communicates with the guide wire lumen 17 in the catheter. Bands 34 of radiopaque material are mounted on the guide wire tube inside the balloon so that the position of the balloon can be observed fluoroscopically, if desired. In a presently preferred embodiment, the balloon assembly is fabricated as a modular unit consisting of balloon 14, guide wire tube 29, marker band 28, spacer 32, and marker bands 34.

The connecting sleeve 31 at the proximal end of the balloon is disposed coaxially about the distal end portion 26 of marker tube and abuts against the distal end of transducer 12, with the outer surface of the sleeve flush with the outer surface of the transducer to provide a smooth transition between the transducer and the balloon. In the embodiment illustrated, marker band 28 is bonded adhesively to the marker tube, but the balloon and transducer can be connected by other suitable means, if desired.

Guide wire tube 29 extends through marker tube 24, with a flow passageway 39 of annular cross-section being formed between the inner wall of the marker tube and the outer wall of the guide wire tube. This passageway communicates directly with the interior of the balloon. It is of relatively large cross-sectional area and is important in providing an unrestricted flow of fluid between the catheter and the balloon.

The proximal end portion of guide wire tube 29 is inserted into the distal end portion of guide wire lumen 17, with the lumens in the catheter and the tube providing a continuous passageway for a guide wire. The tube is bonded to the catheter by heat sealing or fusing. The lumen in the guide wire tube is smaller in diameter than the catheter lumen, and the portion 40 of the catheter lumen immediately proximal to the tube is tapered to provide a smooth transition between the two lumens. The tube has a wall thickness on the order of 0.001 inch, and the taper is formed by inserting a mandrel (not shown) into the tube and applying radial pressure to the catheter shaft to deform the shaft and fill in the region near the tube during the heat sealing process. Mandrels are also inserted into fluid lumen 18 and cable lumen 19 to prevent collapse of those lumens during the sealing process.

The proximal end portion 25 of marker tube 24 is connected to the distal end portion of catheter 11 by a coupling sleeve 41 which fits over the tapered end portion of the catheter shaft. This sleeve is heat sealed or fused to the catheter shaft and is fabricated of a material such as nylon which bonds well with the shaft.

Marker band 27 is disposed coaxially within the distal end portion of coupling sleeve 41, with a matching element or spacer 42 between the two. In a preferred embodiment, these elements are heat sealed together, and the spacer is formed as a co-extrusion with an inner layer of a material such as polyethylene which bonds well with the metal tube and an outer layer of a material such as nylon which bonds well with the coupling sleeve. In a preferred embodiment, the catheter is fabricated as a modular unit consisting of shaft 16, coupling sleeve 41, spacer 42, marker band 27, and cable 22 which is threaded through the cable lumen in the shaft.

The proximal end of the marker tube is spaced from the distal of the catheter, and a plenum chamber 43 is formed between them to provide communication between the flow lumen 18 in the catheter and the flow passageway 39 in the transducer. This chamber is bounded by the inner wall of sleeve 41 and the outer wall of guide wire tube 29, and has an annular cross-section.

An outer sheath 44 extends between the distal end portion of catheter 11 and the proximal end portion of transducer 12 to enclose the region in which the cable emerges from the catheter and is connected to the transducer. It is affixed to the catheter and to the transducer with an adhesive, and the region between the sheath and coupling sleeve 41 is filled with the adhesive to protect the wires connected to the transducer. If desired, further strain relief for the wires can be provided by forming a loop in them.

Manufacture of the device, and therein the method of the invention, are as follows. The catheter, transducer and balloon are each fabricated as a modular unit. The catheter module, or proximal assembly, is illustrated in FIG. 5 and consists of shaft 16, coupling sleeve 41, spacer 42, marker band 27, and cable 22. The transducer module, which is illustrated in FIG. 6, consists of transducer 12 and marker tube 24. The balloon, or distal assembly, is illustrated in FIG. 7 and consists of balloon 14, guide wire tube 29, marker band 28, spacer 32, and marker bands 34.

The transducer and balloon units are assembled together by passing the guide wire tube through the marker tube and cementing marker band 28 to the distal end portion 26 of the marker tube. These units are then connected to the catheter by inserting the proximal end portion of the guide wire tube into lumen 17 and sliding the distal end portion of coupling sleeve 41 over the proximal end portion 25 of marker tube 24. The marker band 27 in the coupling sleeve is cemented to the marker tube, and the guide wire tube is heat sealed to the catheter shaft. The wires in cable 22 are welded to conductive traces on the transducer, and outer sheath 44 is cemented in place to complete the assembly.

Although the invention has been disclosed with specific reference to an angioplasty balloon as the treatment device, any suitable type of treatment or therapy device can be employed. Likewise, rather than cementing the different units together, other types of connectors can be employed. Such connectors might, for example, include bayonet devices or other quick disconnects which would allow the units to be assembled together and separated quickly and easily.

The invention has a number of important features and advantages. It provides an "all-in-one" catheter which provides both imaging and treatment without an exchange of catheters. It does so in a manner which allows the transducer to be positioned proximally of the balloon without unduly restricting the flow of pressurized fluid to and from the balloon. The marker tube serves a dual function in serving as a flow passageway past the transducer as well as providing a visual indication as to the position of the transducer. It reduces balloon inflation and deflation times to less than 15 seconds and eliminates the need for a separate vent tube for the balloon. The modular construction with standardized connectors makes assembly quick and easy, and permits a wide variety of different devices to be connected together.

It is apparent from the foregoing that a new and improved catheter assembly has been provided. While only certain presently preferred embodiments have been described in detail, as will be apparent to those familiar with the art, certain changes and modifications can be made without departing from the scope of the invention as defined by the following claims.

What is claimed is:

1. An imaging catheter assembly, comprising:

a catheter having a guide wire lumen and a fluid lumen which open through a distal end thereof;

an ultrasound imaging transducer positioned distally of the catheter and having a flow passageway; and a plenum chamber providing communication between the fluid lumen in the catheter and the flow passageway in the transducer.

2. The imaging catheter assembly of claim 1 wherein the plenum chamber has a substantially annular cross-section.

3. The imaging catheter assembly of claim 1 further comprising:

a treatment device; and an axially extending guide wire tube affixed to the treatment device;

the guide wire tube being connected to the distal end of the catheter in alignment with the guide wire lumen to form a continuous passageway for a guide wire.

4. The imaging catheter assembly of claim 3 wherein the flow passageway in the ultrasound imaging transducer is in communication with the treatment device.

5. The imaging catheter assembly of claim 3 wherein the ultrasound imaging transducer is located proximal to the treatment device.

6. The imaging catheter assembly of claim 1 wherein the flow passageway in the ultrasound imaging transducer is formed by a metal marker tube which extends coaxially of the ultrasound imaging transducer.

7. The imaging catheter assembly of claim 1 wherein the ultrasound imaging transducer is removably connected to the catheter.

8. A modular imaging/treatment catheter assembly, comprising:

a catheter having a guide wire lumen and a fluid lumen which open through a distal end thereof;

an ultrasound imaging transducer positioned distally of the catheter and having a flow passageway;

a treatment device located distally of the ultrasound imaging transducer and having a guide wire lumen; and a connector for removably coupling the treatment device to the ultrasound imaging transducer such that when the ultrasound imaging transducer and the treatment device are coupled together the guide wire lumen in the treatment device and the guide wire lumen in the catheter form a continuous passageway for a guide wire.

9. The modular imaging/treatment catheter assembly of claim 8 wherein the guide wire lumen in the treatment device is formed by an axially extending tube attached to the treatment device.

10. The modular imaging/treatment catheter assembly of claim 8 wherein the catheter and the ultrasound imaging transducer are removably connected to each other by a second connector.

11. The modular imaging/treatment catheter assembly of claim 8 wherein the treatment device is an angioplasty balloon.

* * * * *